United States Patent [19]

Michaels

[11] 4,304,232

[45] Dec. 8, 1981

[54] UNIT SYSTEM HAVING MULTIPLICITY OF MEANS FOR DISPENSING USEFUL AGENT

[75] Inventor: Alan S. Michaels, San Francisco, Calif.

[73] Assignee: ALZA Corporation, Palo Alto, Calif.

[21] Appl. No.: 115,750

[22] Filed: Jan. 28, 1980

Related U.S. Application Data

[60] Continuation-in-part of Ser. No. 20,521, Mar. 14, 1979, abandoned, which is a division of Ser. No. 862,363, Dec. 20, 1977, abandoned.

[51] Int. Cl.$^3$ .............................................. A61M 7/00
[52] U.S. Cl. .................................... 128/260; 128/270
[58] Field of Search ............... 128/260, 270, 272, 268, 128/213 R, 213 A, 296, 271

[56] References Cited

U.S. PATENT DOCUMENTS

| | | | |
|---|---|---|---|
| 3,017,314 | 1/1962 | Burgeni | 128/296 |
| 3,532,679 | 10/1970 | Steckler | 260/81 |
| 3,760,984 | 9/1973 | Theeuwes | 222/95 |
| 3,865,108 | 2/1975 | Hartop | 128/270 |
| 3,926,188 | 12/1975 | Baker et al. | 128/260 |
| 3,971,376 | 7/1976 | Wichterle | 128/260 |
| 3,977,404 | 8/1976 | Theeuwes | 128/130 |
| 3,987,790 | 10/1976 | Eckenhoff | 128/260 |
| 3,989,589 | 11/1976 | Frisch et al. | 128/36 |
| 3,992,562 | 11/1976 | Denzinger et al. | 526/208 |
| 3,995,631 | 11/1976 | Higuchi et al. | 128/260 |
| 4,008,719 | 2/1977 | Theeuwes et al. | 128/270 |
| 4,016,880 | 4/1977 | Theeuwes et al. | 128/260 |

*Primary Examiner*—Robert W. Michell
*Assistant Examiner*—T. J. Wallen
*Attorney, Agent, or Firm*—Paul L. Sabatine; Edward L. Mandell

[57] ABSTRACT

A system is disclosed for dispensing an useful agent. The system comprises (1) means for storing an agent, (2) an agent stored in the means, (3) means for releasing agent from the system, (4) means for absorbing fluid into the system surrounding the storing means, and (5) means for admitting fluid into the system. In operation fluid is admitted into the system by the admitting means cooperating with the absorbing means, causing it to increase in dimensions and apply force against the storing means, which force urges the storing means to decrease its dimensions and correspondingly dispense agent through the releasing means from the system. Laminates are disclosed useful for manufacturing the system.

13 Claims, 4 Drawing Figures

UNIT SYSTEM HAVING MULTIPLICITY OF MEANS FOR DISPENSING USEFUL AGENT

CROSS-REFERENCE TO RELATED APPLICATION

This application is a continuation-in-part of U.S. Patent Application Ser. No. 020,521 filed on Mar. 14, 1979, and now abandoned which application is a division of U.S. Patent Application Ser. No. 862,363 filed on Dec. 20, 1977 and now abandoned, and benefits is claimed of their filing dates. This application and Ser. No. 020,521 and 862,363 are all assigned to the Alza Corporation of Palo Alto, Calif.

FIELD OF THE INVENTION

This invention pertains to a self-powered system for delivering a beneficial agent to an environment of use.

THE PRIOR ART

Commercially important, manufactured devices useful for dispensing beneficial agent to an environment of use are known to the prior art. For example, U.S. Pat. No. 3,760,984 issued to patentee Theeuwes discloses a device comprising an inner chamber formed of a heat shrinkable polymer carrying on its outer surface an osmotic solute and a distant layer of a polymer permeable to fluid. The device has a means for filling the chamber. In U.S. Pat. No. 3,865,108, Hartop discloses a device consisting of a base with a hollow that holds a receptable. The device can have a highly flexible, water permeable skin that assures the device will not break apart in contact with fluid. A drug is released from the receptacle by cutting it. Neither the skin nor the severed receptacle are disclosed as having rate controlling properties for governing the rate of release from the device. In U.S. Pat. No. 3,987,790, Eckenhoff et al disclose an improvement in osmotic devices consisting of a conduit for filling the devices. In U.S. Pat. No. 3,971,376, Wichterle claims a device consisting of a capsule having unitary walls formed of a substantially non-collapsable material that is exposed to the environment of use. A textile fabric is imbedded in the material for imparting strength and minimizing problems due to poor mechanical properties of the material that occur during fluid uptake. In U.S. Pat. No. 3,995,631, Higuchi et al, disclose a bag bearing on its outer surface a layer of an inorganic solute, and a distant wall formed of a material having part controlled permability to fluid.

While the devices above described are useful for dispensing numerous agents to many environments of use, and while the devices represent a major advancement in the delivery arts, there are instances where an inventively novel, different and useful device also would enjoy wide application. For example, when the device must be placed in an environment of use where a need exists for controlling the amount of agent discharged from the device, a device having a means for interacting with imbibed fluid and swelling to some preselected equilibrium state, thereby producing a force that can be used for driving a known amount of agent from the device, would enjoy immediate acceptance, and also be a valuable contribution in the fields of commerce and science.

OBJECTS OF THE INVENTION

Accordingly, it is an immediate objects of this invention to provide a novel and useful dispensing system for dispensing of an agent to produce a beneficial effect, which system overcomes the aforesaid disadvantages associated with the prior art.

Still another object of the invention is to provide a new dispensing system which system can dispense an agent at a controlled rate for a prolonged period of time in an environment of use having a limited amount of fluid available for use by the system.

Yet another object of the invention is to provide a dispensing system having a means for absorbing fluid and retaining a significant fraction of the fluid within the means as a source of power useful for dispensing an agent from the system.

Still another object of the invention is to provide a system having means for admitting fluid into the system at a controlled rate, means for absorbing the admitted fluid and exhibiting the ability to increase in dimensions over time, which increase can be used as a mechanical, driving power for dispensing agent from the system.

Yet another object of the invention is to provide a dispensing system which system is self-powered, easy to manufacture, and can be used for dispensing beneficial agents to animals including humans, and into other bilogical and nonbiological environments of use.

Another object of the invention is to provide a dispensing system that is empty until filled, and when filled can administer a complete pharmaceutical dosage regimen for a period of time, the use of which requires intervention only for initiation and termination of the regimen.

An additional object of the invention is to provide a laminate useful for fabricating dispensing systems, which systems can function in a plurality of fluid environments.

It is a further object of the invention to provide a novel therapeutic system manufactured as a drug delivery device, which can operate to yield results substantially equivalent to those obtained with a sustained release method of drug administration.

Other objects, features and advantages of the invention will be apparent to those skilled in the art, from the detailed description of this specification, taken in conjunction with the drawings, and the accompanying claims.

SUMMARY OF THE INVENTION

The invention concerns a system for dispensing an agent to an environment of use. The system is manufactured as a dispensing device especially designed for dispensing drug to a biological environment. The system comprises an intermediate, expandable fluid absorbing means made of a hydrophilic material surrounding at least partially an inner collapsible storing means made of an elastomeric material, which contains the agent. The intermediate means is surrounded by a wall formed of a rate controlling material that admits fluid into the system. In operation, the system releases agent in response to the intermediate means absorbing the admitted fluid and expanding, thereby exerting pressure on the inner means which collapses and ejects agent from the system. The invention also concerns a laminate comprising the wall and the inner positioned means.

BRIEF DESCRIPTION OF THE DRAWINGS

In the drawings, which are not drawn to scale, but are set forth to illustrate various embodiments of the invention, the figures are as follows.

In the drawings and specification, like parts in related Figures are identified by like numbers. The terms appearing ealier in the specification, an in the description of the drawings, as well as embodiments thereof, are further described elsewhere in the disclosure.

DETAILED DESCRIPTION OF THE DRAWINGS

Figure 1:
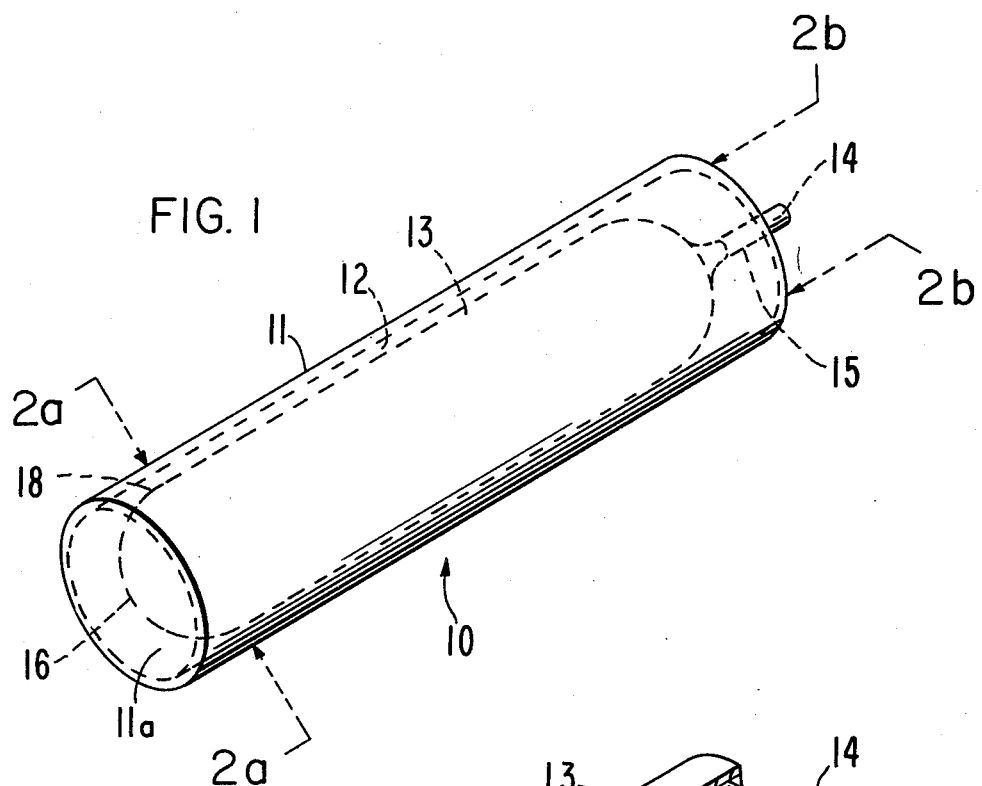
FIG. 1 is a front, elevational view illustrating a device made according to the invention, which depicts a storing means and the fluid admitting means.

Turning now to the drawings in detail, which are an example of a new and useful device for dispensing an agent, including drug, and which example is not to be construed as limiting, one device is illustrated in FIG. 1 by the number 10. In FIG. 1, device 10 comprises means 11 for admitting fluid into device 10. Means 11 is a wall or housing, also indentifiable as 11, that is shaped, sized and adapted for placing device 10 in the preselected environment of use. Wall 11 surrounds and defines an internal space 11a designed for receiving and housing means 13. Wall 11 is made from a material that controls the amount of an exterior fluid present in the environment of use that can enter device 10. The material forming wall 11, in addition to governing the volume of fluid admitted into device 10, also imparts physical integrity and structure to device 10 throughout the dispensing period. Means 13, seen in dashed lines in FIG. 1, is designed for storing an active agent, not shown, which agent in a presently preferred embodiment is a drug. Means 13 is manufactured as a container, also identified as 13 and seen as dashed lines in FIG. 1. Container 13 has a lead end 15 that forms and defines means 14 for releasing agent from container 13 to the exterior of device 10. Container 13 is made from a material that can house a beneficial agent substantially free from any adverse effects on the agent. The container also can house the agent over a prolonged period of time sheltered from any possible adverse actions present in the environment of use. Means 14, which is preferrably formed during the manufacture of container 13, can also be described as a passageway, and it has internal dimensions preselected for assisting in governing the rate of release of agent from device 10. Container 13 has a trailing end 16 and an exterior surface surrounded in whole or in at least a part by means 12. Container 13 is made of an elastomeric, or other low-modulus material, that can decrease its dimensions over time, and more particularly, collapse in response to pressure applied against the exterior surface of container 13. FIG. 1 also illustrates means 12, seen in dashed lines, and in spaced relation with wall 11 and container 12.

Means 12, as seen in housing 11a, is positioned between the inside surface of wall 11 and the exterior surface of container 13. Means 12 is made of a hydrophilic, swellable material, designed for absorbing and reversibly retaining fluid. This physical-chemical property causes 12 to increase its space occupying dimensions, which action is transmitted as an applied force against container 13. This force correspondingly diminishes the dimensions of container 13 and urges the container to dispense agent from the device. The increase in dimensions of the swellable material occurs in cooperation with (1) wall 11 that regulates the volume of fluid admitted and available in the device, with (2) container 13 that collapses in response thereto, and with (3) the passageway that assists in governing release from the device. The structural members of the device act as a unit system to achieve the desired result.

Figure 2:
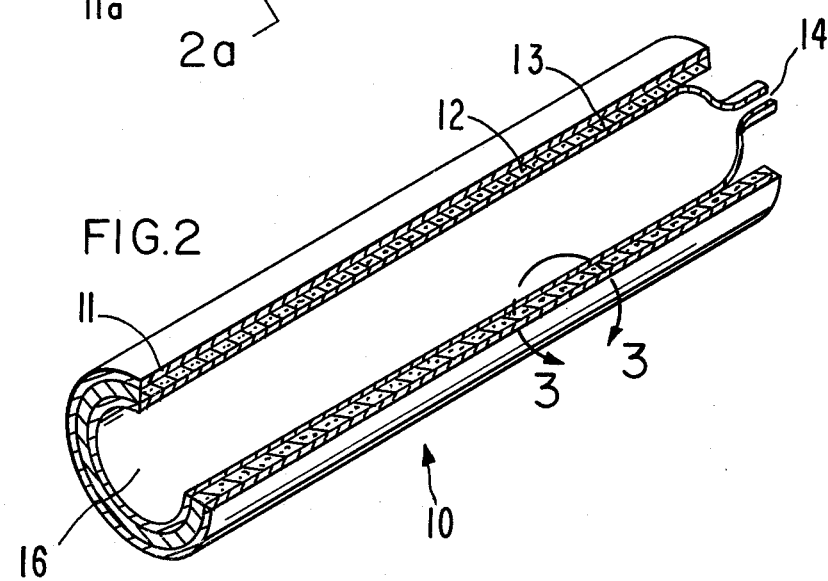
FIG. 2, taken in conjunction with FIG. 1, illustrates the device in opened-section along 2a–2a and 2b–2b, for illustrating the structure of the device.

FIG. 2 illustrates device 10 of FIG. 1 in opened-section seen in cross-section along lines 2a–2a and 2b—2b of FIG. 1. FIG. 2 depicts the integral structure of device 10 comprising wall 11, an outer lamina forming the housing of device 10, which lamina has a surface, that faces the environment of use when device 10 is placed therein, aand an inner surface faced in laminar arrangement with means 12. Means 12, described above, and it is the structural equivalent of an intermediate lamina hving a surface faced towards lamina 11 and surface faced towards the wall of container 13. The outer surface of the wall of container 13 is essentially in laminar arrangement with the intermediate and outer members forming device 10.

Figure 3A:
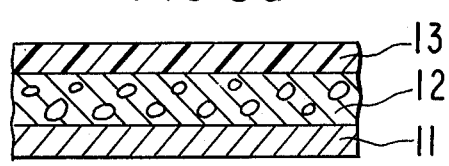
FIGS. 3a and 3b illustrate the laminate defining the structural members of the device, taken through 3—3 of FIG. 2.
Figure 3B:
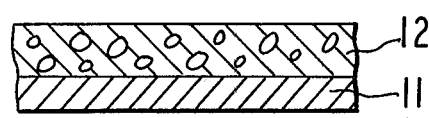

FIG. 3a and 3b illustrate views taken through 3—3 of FIG. 2. FIG. 3 shows a superposed laminar arrangement comprising lamina 11 formed of a material that regulate the passage of fluid and which material maintains its physical and chemical integrity throughout the dispensing period positioned adjacent to lamina 12. Lamina 12 is formed of a swellable, hydrophilic polymer that can imbibe and reversibly retain aqueous and biological fluids positioned adjacent to the wall of container 13. The wall of container 13 is the functional equivalent of a lamina, and 13 is formed of an elastomeric material that collapses in operation to produce the intended results. FIG. 3b shows a novel laminate provided by the invention comprising laminae 11 and 12.

While FIGS. 1 through 3 are illustrative of various systems that can be made according to the invention, it is to be understood these systems are not to be construed as limiting, as they can take a wide variety of shapes, sizes and forms adapted for delivering an agent including drug to many and varied different environments of use. For example, system 10 can be manufactured for dispensing drug to animals, which term includes warm-blooded mammals, humans, household, farm, sport and zoo animals. The devices can also be used for dispensing drugs to avians, fishes and reptiles. Dispensing device 10 can be sized, shaped and adapted for dispensing drug to body cavities and body openings, and for uses including oral administration, intramuscular implants, intrauterine, vaginal, cervical, rectal, nasal, ear, and dermal applications. Device 10 also can be used as an artificial gland, and for arterial and venous administration of drug. The device can be made for use in homes, hospitals, nursing homes, clinics, ships, laboratories, factories and the like.

DETAILED DESCRIPTION OF THE INVENTION

Device 10, as used for the purpose of the invention, consists of a wall 11, or housing, made of a substantially polymeric material. This material, is preferably rigid, and it permits pressure to be exerted against it without any major change in its shape or dimensions, thereby assuring that pressure generated in device 10 is exerted against container 13. Housing 11 is made from a semipermeable polymer that regulates the passage of fluid into the device. The semipermeable polymers suitable for forming the wall are polymers that display selective water permeability. The phrase selective water permeability, as used herein, denotes polymers that are permeable to the passage of water and essentially impermeable to the passage of solute. The semipermeable polymers act in cooperation with the hydrophilic hydrogels in the device and govern the passage of water through the wall into the device. Generally, the semipermeable polymer will have a water permeability pf 0.01 to 10 cc/cm$^2$/hr or/day or longer. Typical semipermeable polymers suitable for forming the wall include cellulose acylate, cellulose diacylate, cellulose triacylate, cellulose acetate, cellulose diacetate, cellulose triacetate, cellulose polymes having at least one acyl group with the remaining degrees of substitution on the anhydroglucose units selected from hydrogen, hydroxal and hydrocarbyl. The volume of water that passes through the wall can be further controlled by selecting cellulose polymers possessing a high degree of substitution, for example, the polymer has undergone esterification or esterification, particularly acylation towards completition, by decreasing or increasing the size of substituting groups on the cellulose polymer, and by selecting hydrophobic and hydrophilic groups as substitutients on the polymer forming wall 12. Additional water semipermeable polymers that can be used include polymeric epoxides, semipermeable membranes made from copolymers of an alkylene oxide and alkyl glycidyl ether, semipermeable polyurethanes, polyamides, polyacrylic esters, membranes of ionically associated polyelectrolytes, polymers formed by the coprecipitation of a polycation and a polyanion, semipermeable derivatives of polystyrene such as poly(sodium styrenesulfonate) and poly(vinlbenzyltrimethlammonium chloride), polyaromatics, and the like. Semipermeable polymers are disclosed in U.S. Pat. Nos. 3,133,132; 3,173,876; 3,276,586; 3,541,005; 3,543,142; and 3,845,770.

Wall 11 also can be made from a microporous polymeric material whose pore size regulates the volume of fluid that enters the device. Representative microporous polymers have a pore size of up to several hundred microns, down to several angstroms or smaller. Typical microporous polymers include microporous polyesters, polycarbonates, microporous polyamides, polyvinyl chloride with a pore size of about 5A or less to 150 microns, microporous polyamides, polyimides, polybenzimidazoles, acetal polymers, phenolic polesters, and the like. Procedures for preparing microporous polymers are described in Synthetic Polymer Membranes by R. E. Kesting, Chapters 4 and 5, 1971, published by McGraw Hill, Inc.; in Chemical Reviews, Vol. 18 pages 373 to 455; 1934; Polymer Eng. and Sci., Vol. 11, pages 811 to 829, 1971; and in U.S. Pat. Nos. 3,565,259; 3,615,024; 3,751,536; 3,801,692; 3,852,244; 3,849,528; and 4,160,452.

Wall 11, in an inventive embodiment, also can be made from a microporous polymer whose pores are filled with a water permeable material that regulates the passage of water into the device. Generally, the microporous polymer has from 5 to 50% pores interconnected through tortuous paths which extend from one surface of the wall to the other surface of the wall. Generally, polymers having a pore size of from 10 angstroms to 10 microns can be used for manufacturing the device. The microporous polymers can embrace structures characteristic of microporous polyolefins, polyamides, polycarbonates, polyesters, polysytrenes, polysulphones, polyimides, polyvinyls, polyarylenes, polyaldehydes, polyarylates, polyhaloolefins, polyacetals, polyacrylates, polyurethanes, the homopolymers and copolymers thereof, and the like.

The pores of the polymer can be filled with a hydrophilic, or a hydrophobic material that exhibits selective permeability to the passage of water. Representative materials include glycerin, ethylene glycol, propylene glycol, methyl cellulose mixed with water, mixtures of propylene glycol monostearate and oils, gum tragacanth, polyoxyethylene stearate, alkylene diols wherein the alkylene has 2 to 10 carbons such as poly(1,5)-pentanediol, polyesters of alkylene glycols and a monobasic or dibasic acid such as ethylene glycol diacetate, and the like.

The material can be added to the pores by immersion of a microporous polymeric film in a bath containing the material to let it fill the micropores. The material can be added to the polymer during casting of the polymer. For example, pulverized solid, cross-linked polymethylmethacrylate, an insoluble swellable polymer that allows for the presence of water, is added to a polymer dissolved in a solvent, such as ethylene vinyl acetate copolymer in methylene chloride, with the copolymer cast and the solvent evaporated to leave a film that function with microporous characteristics. The micropores of a polymeric film, for example a film of polyhexamethylene adipamide, can be charged by spreading and working into the pores hydroxyethyl methacrylate-ethylene glycol dimethacrylate dissolved in diacetine, followed by evaporation and wiping the film clean. The micropores also can be filled with a hydrogel cross-linked in the pores. For example, the hydrogel can consist of a sparingly cross-linked copolymer of a monoester of an olefinic acid and a polyfunctional alcohol having an esterifiable hydroxyl group and at least one additional hydrophilic functional group, with a diester of an olefinic acid and an alcohol having at least two esterifiable hydroxyl groups. Examplary olefinic acids include acrylic and methacrylic acids, and exemplary alcohols include polyalkylene glycol, trialkanolamine, polyvinyl alcohol, and the like. The micropores of a polymer for example polyvinyl chloride can be filled with a hydrogel by copolymerizing a glycol and a mono or di(meth)acrylate in a solvent in the pores, followed by irradiating with x or gamma rays. The micropores of a polymer also can be filled with the hydrophilic polymers disclosed later in the specification. Generally, the microporous wall will have a thickness, depending on the device and its use, of from about 0.01 mm to 7 mm, or more.

Representative of swellable, hydrophilic polymers, suitable for forming means 12, are for example, hydrogels, lightly cross-linked, predominately linear polymers, but also including hydrophilic polymers having dimensional networks, such cross-links formed in both structures by covalent or ionic bonds. These polymers interact and absorb biological and aqueous fluids and swell or expand to some equilibrium state. The polymers swell to a very high degree without dissolution, usually exhibiting a 5 to 50 fold volume increase. In an embodiment, the invention provides devices using hydrogels that can be cross-linked to a preselected density, which makes it possible to control the volume increase of the hydrogel to some equilibrium value. This increased volume can be equal to or greater than the volume of the filled container, thereby assuring complete discharge of agent from the container. The swellable hydrophilic polymers suitable for the present applications include poly(hydroxyalkyl methacrylates); poly(acrylamide); poly(methacrylamide) and derivatives; poly(N-vinyl-2-pyrrolidone); anionic and cationic hydrogels; poly(electrolyte) complexes; cross-linked protein polymers; poly(vinyl alcohol) having a low acetate residual and cross-linked with glyoxal, formaldehyde or glutaraldehyde; poly(saccharide); methylcellulose cross-linked with a dialdehyde; a mixture of agar and sodium carboxymethylcellulose; swellable starch; a water-insoluble, water swellable copolymer produced by forming a dispersion of finely divided copolymer of maleic anhydride with styrene, ethylene, butylene or isobutylene cross-linked with from 0.001 to about 0.5 mole of a polyunsturated cross-linked agent per mole of maleic anhydride in the copolymer as disclosed in U.S. Pat. No. 3,989,589; water-swellable, lightly cross-linked hydrogels made of cross-linked polymers of N-vinyl lactams and alkyl lactams made according to procedures in U.S. Pat. Nos. 3,532,679 and 3,992,562; and the like. Generally, lamina 12 will have a thickness of about 0.001 mm to 7 mm, and in a presently preferred operative embodiment, it will have an expanded or swelled thickness state approximately equal to the internal diameter of container 13, for producing a complete collapse of container 13 and discharge of agent from device 10.

Representative of materials suitable for manufacturing container 13 are materials that can be designed into a shaped container, structured as an elastomeric tube or capsule, which collapses in response to externally applied pressure, thereby dispensing agent or drug. Typical elastomeric polymers include natural rubber, often identified by the synonyms poly(2-methyl-1,3-butadiene) and cis-1,4-polyisoprene, gutta percha or trans-polyisoprene, cyclized rubber, silicone rubber, synthetic isoprene rubber, butadiene rubber, copolymeric styrene-butadiene rubbers, nitrile rubber, chloroprene rubber, ethylene-propylene rubbers, butyl rubbers, and the like. These elastomric materials are disclosed in *Handbook of Common Polymers*, by Scott and Roff, Sections 29 through 40, 1971, published by the Chemical Rubber Co., Cleveland, Ohio. Container 13, formed of the above representative materials, can have a wall of varying thickness, usually about 0.001 mm to 7 mm, or more depending on the container and the use of device 10. Container 13 is manufactured with a passageway for dispensing agent or drug, and it can be made to form a passageway when device 10 is in the environment of use. Passageway 14 will have a cross-section of 1 to 20 mils. When passageway 14 is formed in the environment of use, it is closed with a water-soluble plug of an erodible material, such as noncross-linked poly(vinyl alcohol), gelatin or the like that erodes to form the passageway. The end of container 13 including passageway 14 can also receive a tube or conduit, not shown, for transporting agent dispensed from the device to a receiving site located away from the device.

Exemplary useful or active agents that can be administered according to the spirit of the invention include agents that benefit the environment, manufacture and science. The term agent includes algicides, anti-oxidants, air purifiers, biocides, bactericides, catalysts, chemical reactants, cosmetics, disinfectants, drugs, fungicides, flavoring agents, foods, food supplements, fertility inhibitors, fermentation agents, fertility promoters, germicides, insecticide, microorganism alternators, nutrients, pesticides, plant growth promoters, plant growth inhibitors, preservating agents, slimicides, surfactants, sterilization agents, sex sterilants, vitamins, and other like agents that benefit animals and man.

Exemplary drugs that can be administered according to the spirit of the invention include locally and systemically acting drugs. These drugs include a member selected from the group consisting of physiologically and pharmacolgically acting drugs such as gastrointestinal administrable drugs, central nervous system acting drugs, hypnotic, sedative, psychic energizer, tranquilizer, anticonvulsant, anti-parkinson, muscle relaxant, analgesic, antipyretic, anti-inflammatory, anesthetic, antispasmodic, antimicrobial, antiviral, antiulcer, hormonal, sympathomimetic, diuretic, hypoglycemic, vitamins, contraceptive, and opthalmic drugs. These beneficial drugs and their does amounts for humans are known to the art in *Drills' Pharmacology in Medicine*, edited by DiPalma, Joseph R., 1965, published by McGraw-Hill Book Company, New York, in *Pharmacological Basis of Therapeutics*, by Goodman and Gilman, 4th Edition, 1970, published by MacMillian Co., London, and in U.S. Pat. No. 3,977,404, which patent is assigned to the ALZA Corporation of Palo Alto, Calif., the assignee of this application. The drug in the container can be mixed with a pharmaceutically acceptable liquid such as water, saline, cottonseed oil, sesame oil, ethylene oleate, isopropyl myristate, propylene glycol, and the like. The drug can be present in solution, in semi-solid or paste formulation, in a thixotropic state and the like, which form permits controlled dispensing of drug from the device. Pharmaceutically acceptable carriers and the like are known to the art in *Remington's Pharmaceutical Science*, 14th Edition, pages 1461 to 1762, 1970, published by the Mack Publishing Company, Easton, Pennsylvania.

The following examples are illustrative of the present invention, and they should not be considered as limiting the scope of the invention in any way, as these examples and other equivalents thereof will become more apparent to those versed in the art in the light of the present disclosure, the drawings and the accompanying claims.

EXAMPLE 1

An improved dispensing device embracing the structural members acting together is manufactured as follows: first, a cylindrical shaped container 2.33 cm long, 3.81 inside diameter and 4.67 mm outside diameter, is injection molded at 180° C., at 77–84 kg/cm$^2$, from the elastomeric copolymer styrene-butadiene. Next, a mandrel is inserted into the container, and this assembly placed into a two-piece cavity mold. Next, the mold charged with a mixture of 30 parts of ethyleneglycol monomethacrylate containing 0.12 of ethyleneglycol dimethacrylate, and 10 parts of 0.13% aqueous solution of sodium disulfate in aqueous ethanol. This mixture polymerizes at 30° C., and after 20 minutes following equilibration to room temperature the mold is removed.

Next, a solution of cellulose acetate in acetone, 15 wt% with an acetyl content of 39.8%, is prepared and the mandrelsupported hydrogel coated containers dipped into the solution 20 times for 1 minute per dip, with an intervening 15 minute drying period. Following this dipping, the systems are dried at 60° C. for 15 days. This procedure applies a 0.65 mm of the rate controlling wall onto the hydrogel lamina.

In operation, the above prepared system, when placed in a fluid environment, makes available improved controlled delivery of an agent. This is achieved by the wall acting in cooperation with the hydrogel lamina. That is, the wall permits the passage of fluid at a controlled rate into the system, which fluid is imbibed and absorbed at a controlled rate by the hydrogel. This double control provided by these two lamina operating as a unit laminate leads to the controlled expansion of the hydrogel lamina generating pressure that is applied against the exterior surface of the container. The pressure causes the container to be squeezed inwardly at a controlled rate and correspondingly dispense agent through the passageway at a controlled rate over time. Also, by preselecting the elastomeric material used for fabricating the container, an additional control is provided by the system.

EXAMPLE 2

The procedure of Example 1 is repeated with all conditions as set forth, except that the mold is filled with a cross-linked, swellable, hydrophilic polymer forming composition consisting essentially of 30 parts by weight of hydroxyethyl methacrylate, 0.1 part by weight of cross-linking agent ethylene dimethacrylate, and 8 parts by weight of a 1–2% solution of sodium pyrosulfate. The mold is heated to about 30°–35° C. for about 15–25 minutes, and then for 5–10 minutes at about 100° C. In this example, the semipermeable polymer is cellulose acetate having an acetyl content of 32% applied by using a Wurster air suspension machine.

EXAMPLE 3

The procedure of Example 1 is repeated with all conditions as described except the wall coated onto the hydrogel is a microporous polymer with micropores and micropaths therethrough that regulate fluid intake into the system.

EXAMPLE 4

Representative of the structure of a therapeutic system made according to the invention that can be used for orally administering a drug is as follows: (1) a rigid semipermeable lamina manufactured with an opening laminated onto, (2) a lamina of poly(vinyl alcohol) cross-linked with glyoxal directly laminated onto (3) a container shaped and sized like a 000 capsule with a single passageway for releasing drug and formed of natural rubber, with a drug formulation in the container comprising (4) tetracycline hydrochloride in polyethylene glycol 200.

Although the foregoing invention has been described in detail by way of illustration of presently preferred embodiments and examples for the purpose of clarity of understanding, it will be understood that certain changes and modifications may be practiced without departing from the scope and spirit of the invention.

I claim:
1. An agent dispensing device comprising:
 (a) a container for storing a beneficial agent, said container formed of an elastomeric polymer that is changeable from an agent storing capacity to a substantially emptied capacity over time;
 (b) a wall surrounding and defining an internal space that houses the container, the wall formed of a material selected from the group consisting of a semipermeable and microporous polymer that have selective fluid permeability and governs the passage of fluid into the device at a controlled rate, maintains the physical integrity of the device, and lets pressure be exerted against it, thereby assuring that pressure generated in the device is applied inwardly against the container;
 (c) a passageway communicating with the container and the exterior of the device for dispensing agent from the device, said passageway having internal dimensions that assist in governing the rate of release of agent from the device;
 (d) a lamina positioned between the wall and the container in the device, said lamina surrounding the container and formed of a material that absorbs and retains an exterior fluid admitted into the device, and is capable of changing in size at a controlled rate in response to absorbed and retained fluid; and
 (e) wherein, when the device is in operation, fluid is admitted into the device at a rate controlled by the wall acting in cooperation with the lamina that absorbs and retains the fluid, causing the lamina to increase in size at a controlled rate and apply pressure against the container, which urges the container to squeeze inwardly at a corresponding rate and dispense agent through the passageway to the exterior of the device at a combined rate governed by the wall, lamina, container and the internal dimensions of the passageway.

2. The agent dispensing device according to claim 1, wherein, the wall is formed of member selected from the group consisting of cellulose acylate, cellulose diacylate and cellulose triacylate.

3. The agent dispensing device according to claim 1, wherein, the device is sized, shaped and adapted for use in the rectal passageway.

4. The agent dispensing device according to claim 1, wherein, the lamina for absorbing and retaining fluid is a swellable, hydrophilic, cross-linked polymer.

5. The agent dispensing device according to claim 1, wherein, the lamina for absorbing and retaining fluid is formed of a member selected from the group consisting of lightly cross-linked poly(hydroxyalkyl methacrylate), poly(acrylamide), poly(methacrylamide), poly(N-vinyl-2-pyrrolidone), anionic and cationic hydrogels, poly(electrolytes) and protein polymers.

6. The agent dispensing device according to claim 1, wherein, the container houses an agent that is a drug, which drug is present in solution, in semi-solid, or in a thixotropic formulation.

7. The agent dispensing device according to claim 1, wherein, the container is formed of a member selected from the group consisting of natural rubber, gutta percha, cyclized rubber, silicone rubber isoprene rubber, butadiene rubber, styrene-butadiene rubber, nitrile rubber, chloroprene rubber, ethylene-butylene rubber, and butyl rubber.

8. The agent dispensing device according to claim 1, wherein, the container is formed with the passageway, and the lamina for absorbing and retaining fluid is a swellable, hydrophilic polymer and has a surface in contact with the container.

9. The agent dispensing device according to claim 1, wherein, the container houses an agent that is a drug, said drug a member selected from the group consisting of locally and systemically acting drugs.

10. The agent dispensing device according to claim 1, wherein, the device is sized, shaped and adapted for oral use and the dispensing of agent in the gastrointestinal tact.

11. The agent dispensing device according to claim 1, wherein, the passageway is connected to a conduit to transport dispensed agent to a receptor distant from the device.

12. The agent dispensing device according to claim 1, wherein, the device is sized, shaped and adapted for dispensing agent in a vagina.

13. The agent dispensing device according to claim 1, wherein, the device is sized, shaped and adapted for uses as an implant.

* * * * *